United States Patent
Hodorek

(10) Patent No.: US 8,403,985 B2
(45) Date of Patent: Mar. 26, 2013

(54) JOINT SPACER IMPLANT

(75) Inventor: Robert A. Hodorek, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 727 days.

(21) Appl. No.: 11/265,652

(22) Filed: Nov. 2, 2005

(65) Prior Publication Data

US 2007/0100450 A1   May 3, 2007

(51) Int. Cl.
*A61F 2/08* (2006.01)

(52) U.S. Cl. .................. 623/14.12; 623/13.12

(58) Field of Classification Search ....... 623/13.12–13.2
See application file for complete search history.

(56) References Cited

U.S. PATENT DOCUMENTS

| | | | |
|---|---|---|---|
| 3,867,728 A * | 2/1975 | Stubstad et al. ........... | 623/17.16 |
| 3,987,497 A * | 10/1976 | Stoy et al. ................. | 623/13.15 |
| 4,932,969 A | 6/1990 | Frey et al. | |
| 6,001,100 A * | 12/1999 | Sherman et al. ........... | 606/72 |
| 6,206,927 B1 | 3/2001 | Fell et al. | |
| 6,283,996 B1 | 9/2001 | Chervitz et al. | |
| 6,629,997 B2 * | 10/2003 | Mansmann ................ | 623/14.12 |
| 6,679,914 B1 | 1/2004 | Gabbay | |
| 7,066,960 B1 | 6/2006 | Dickman | |
| 7,291,169 B2 | 11/2007 | Hodorek | |
| 7,867,280 B2 | 1/2011 | Goble et al. | |
| 8,238,060 B2 | 8/2012 | Yamada et al. | |
| 2001/0004710 A1 * | 6/2001 | Felt et al. .................. | 623/17.12 |
| 2001/0027343 A1 * | 10/2001 | Keller ........................ | 623/11.11 |
| 2002/0022884 A1 | 2/2002 | Mansmann | |
| 2002/0029083 A1 | 3/2002 | Zucherman et al. | |
| 2002/0123750 A1 * | 9/2002 | Eisermann et al. ............ | 606/69 |
| 2002/0173855 A1 | 11/2002 | Mansmann | |
| 2002/0183845 A1 | 12/2002 | Mansmann | |
| 2003/0055500 A1 | 3/2003 | Fell et al. | |
| 2003/0055501 A1 | 3/2003 | Fell et al. | |
| 2003/0060882 A1 | 3/2003 | Fell et al. | |
| 2003/0060883 A1 | 3/2003 | Fell et al. | |
| 2003/0060884 A1 | 3/2003 | Fell et al. | |
| 2003/0060885 A1 | 3/2003 | Fell et al. | |
| 2003/0060888 A1 | 3/2003 | Fell et al. | |
| 2003/0167092 A1 * | 9/2003 | Foley ......................... | 623/17.11 |
| 2004/0006393 A1 | 1/2004 | Burkinshaw | |
| 2004/0093081 A1 * | 5/2004 | Nilsson et al. .............. | 623/13.18 |
| 2004/0133275 A1 | 7/2004 | Mansmann | |
| 2004/0199250 A1 | 10/2004 | Fell | |

(Continued)

FOREIGN PATENT DOCUMENTS

EP  0505634 A1  9/1992
FR  2747914 A1  10/1997

(Continued)

OTHER PUBLICATIONS

U.S. Appl. No. 10/901,941, filed Jul. 28, 2004, Justin et al.

(Continued)

*Primary Examiner* — David Isabella
*Assistant Examiner* — Ann Schillinger
(74) *Attorney, Agent, or Firm* — Schwegman, Lundberg & Woessner P.A.

(57) ABSTRACT

A spacer implant designed for placement between the bones of a joint, which includes soft tissue components. The spacer includes a spacer body positionable between the bones and defined by an outer periphery. The spacer also includes at least one tether. Each of the tethers has a first end fixed to the spacer body and a second end extending outwardly from the outer periphery of the spacer body. The second end of each of the tethers is adapted to be fastened to any of the bones or the soft tissue components of the joint.

12 Claims, 4 Drawing Sheets

U.S. PATENT DOCUMENTS

| | | |
|---|---|---|
| 2004/0247641 A1 | 12/2004 | Felt et al. |
| 2005/0015153 A1 | 1/2005 | Goble et al. |
| 2005/0287187 A1 | 12/2005 | Mansmann |
| 2006/0178744 A1* | 8/2006 | de Villiers et al. ......... 623/17.13 |
| 2007/0100449 A1* | 5/2007 | O'Neil et al. .............. 623/13.14 |
| 2007/0179607 A1 | 8/2007 | Hodorek et al. |
| 2007/0224238 A1 | 9/2007 | Mansmann et al. |
| 2008/0051889 A1 | 2/2008 | Hodorek |

FOREIGN PATENT DOCUMENTS

| | | |
|---|---|---|
| FR | 2803191 A1 | 7/2001 |
| WO | WO2004/032987 A1 | 4/2004 |
| WO | WO2004/064693 A1 | 8/2004 |
| WO | WO2006/060555 A1 | 6/2006 |

OTHER PUBLICATIONS

U.S. Appl. No. 10/901,935, filed Jul. 28, 2004, Goble et al.

The International Search Report and Written Opinion mailed in related International Application No. PCT/US2006/060436 on Jul. 26, 2007.

"International Application Serial No. PCT/US2006/060436, International Preliminary Report on Patentability dated May 6, 2008", 5 pgs.

* cited by examiner

JOINT SPACER IMPLANT

BACKGROUND

The present invention relates to prosthetic devices for replacing worn articular cartilage and restoring space between bones in a joint.

The knee joint is the union between the femur and the tibia. The knee joint, generally, is formed of a pair of condyles (medial and lateral) located at the distal portion of the femur and a tibial plateau located at the proximal end of the tibia and shaped to mate with the pair of condyles. The knee joint is considered a bi-compartmental joint having a medial compartment, which is defined by the medial condyle and its mating portion of the tibial plateau, and a lateral compartment, which is defined by the lateral condyle and its mating portion of the tibial plateau. A healthy knee joint includes a well-proportioned amount of articular cartilage between the articulating surfaces of the condyles and tibial plateau in each compartment. This cartilage, often referred to as the medial meniscus and lateral meniscus, serves as a cushion between the articulating surfaces of the femoral condyles and the tibial plateau.

Osteoarthritis is a common form of arthritis occurring in the joint and brought about by trauma to the joint, genetic predisposition, and/or aging. Osteoarthritis is characterized by a progressive deterioration and loss of the articular cartilage in the joint. In the case of osteoarthritis in the knee, the degeneration of the articular cartilage in the two compartments of the knee is often uneven resulting in an ill-proportioned amount of cartilage in the compartments. In other words, one compartment of the knee may be left with significantly less articular cartilage. The absence of sufficient cartilage in a compartment leaves the patient lacking proper cushion and spacing between the bones in that compartment. Ultimately, this may cause the femur to tilt downward toward the more heavily-eroded compartment, thereby resulting in a varus or valgus presentation of the knee. As a further consequence, either of these presentations may place added pressure on the already deteriorated cartilage thereby exacerbating and, perhaps, accelerating further degeneration of the articular cartilage remaining in the compartment. Practically, the lack of proper cushioning between the articulating surfaces of the femur and tibia can cause the patient remarkable pain and discomfort.

Attempts have been made to treat this condition by replacing the articulating surfaces via a total or uni-condylar knee replacement. Although successful, these methods may be significantly invasive and may require the removal of a significant amount of bone structure. Alternatively, prosthetic spacers have been proposed that may be implanted in a single compartment of the knee to restore the proper spacing. These prosthetic spacers are often called "uni-spacers." Uni-spacers are typically rigid constructs formed of metal, such as cobalt chrome.

There is a need for a joint spacer that can be implanted into a joint to replace worn articular cartilage, restore joint spacing, and alleviate pain without the need for significant bone remodeling.

SUMMARY

The present invention provides a prosthetic device for replacing worn articular cartilage and restoring space between bones in a joint. In one form, the spacer implant is designed for placement between the bones of a joint, which includes soft tissue components. The spacer includes a spacer body positionable between the bones and defined by an outer periphery. The spacer also includes at least one tether. Each of the tethers has a first end fixed to the spacer body and a second end extending outwardly from the outer periphery of the spacer body. The second end of each of the tethers is adapted to be fastened to any of the bones or the soft tissue components of the joint.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein.

Figure 1:
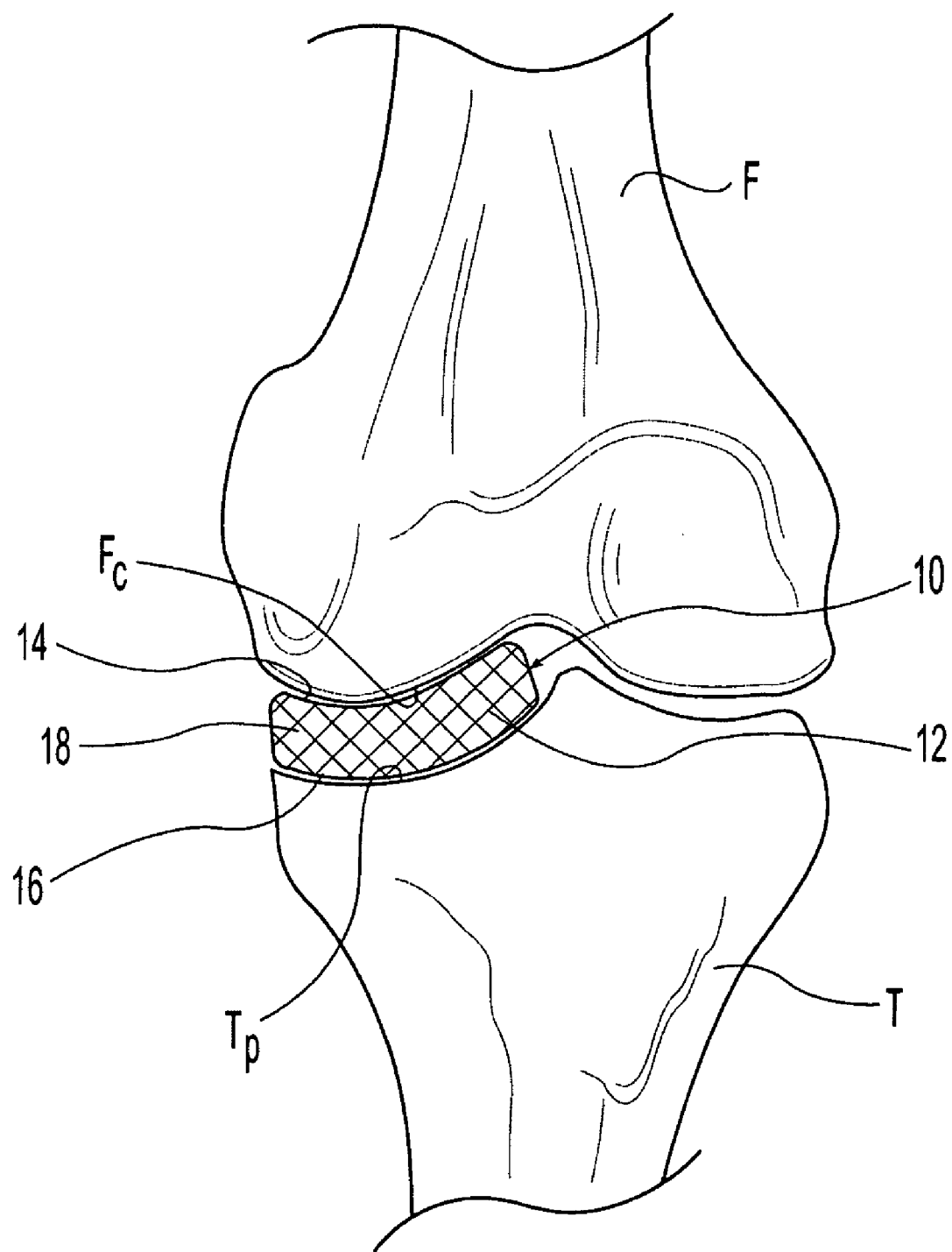
FIG. 1 is an anterior aspect of a knee with a joint spacer implant, according to one embodiment of the present invention, positioned between a femoral condyle and the tibial plateau.

Corresponding reference characters indicate corresponding parts throughout the several views. Although the drawings represent embodiments of the present invention, the drawings are not necessarily to scale and certain features may be exaggerated in order to better illustrate and explain the present invention. Although the exemplification set out herein illustrates embodiments of the invention, in several forms, the embodiments disclosed below are not intended to be exhaustive or to be construed as limiting the scope of the invention to the precise forms disclosed.

DETAILED DESCRIPTION

The embodiments hereinafter described are not intended to be exhaustive or limit the invention to the precise forms disclosed in the following description. Rather the embodiments are chosen and described so that others skilled in the art may utilize its teachings.

Referring first to FIG. 1, spacer 10 of the present invention is shown implanted between the femur F and tibia T of a knee joint. More particularly, spacer 10 is positioned in the lateral compartment of the knee between femoral condyle $F_c$ and tibial plateau $T_p$. Spacer 10 includes spacer body 12, which is defined by femoral bearing portion or surface 14, tibial bearing portion or surface 16, and outer periphery 18 extending between femoral bearing portion 14 and tibial bearing portion 16. As illustrated, spacer body 12 is sized and shaped to fit in a single compartment of the knee between femoral condyle $F_c$ and tibial plateau $T_p$.

Figure 2:
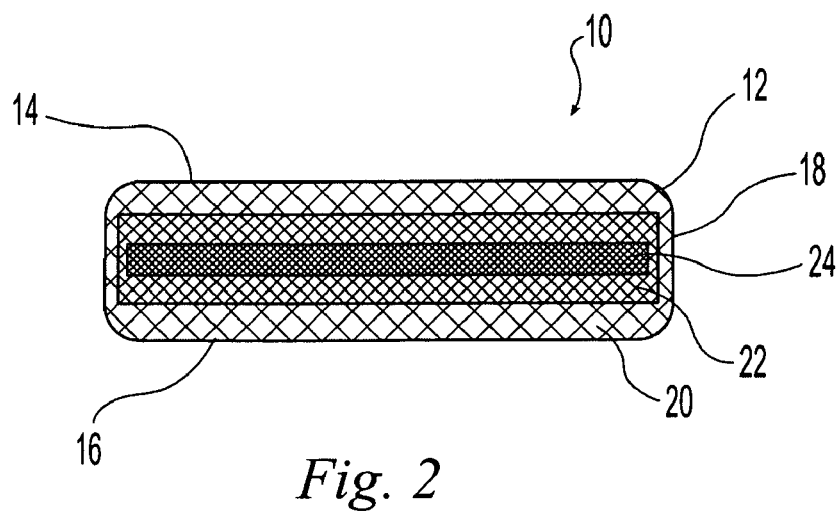
FIG. 2 is a sectional view of the joint spacer implant of FIG. 1.
Figure 2A:
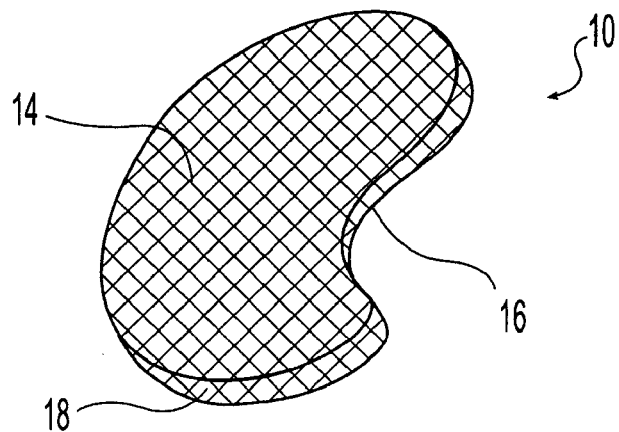
FIG. 2A is a perspective view from the femoral bearing side of the joint space implant of FIG. 1.

Turning now to FIGS. 1, 2 and 2A, spacer body 12 is formed of a plurality of layers, including exterior layer 20 and core layer 24. Exterior layer 20 is the outermost layer of spacer body 12, while core layer 24 is the innermost layer of spacer body 12. Spacer body 12 also includes intermediate layer 22 disposed between exterior layer 20 and core layer 24. Each of layers 20, 22 and 24 are formed of materials having different material properties such that the layers vary from one another in strength and/or hardness. That is, the layers vary in their capacity to resist force and abrasion, thereby minimizing deformation, breakage and/or wear. For instance, in the embodiment illustrated in FIGS. 1, 2 and 2A, the layers increase in strength and/or hardness moving from exterior layer 20 to core layer 24.

More particularly, exterior layer 20 provides an articulating surface against which femoral condyle $F_c$ and tibial plateau $T_p$ can bear and slide. Exterior layer 20 may be made of any material that can provide a smooth, preferably slick, surface for articulation. In one embodiment, exterior layer 20 is relatively flexible and has a strength and/or hardness that is less than that of intermediate layer 22 and core layer 24. For instance, exterior layer 20 may be composed of hydrogel. Hydrogels suitable for forming exterior layer 20 may include, for example, polyvinyl alcohol hydrogels, polyvinyl pyrolidone hydrogels, and polyacrylic acid hydrogels. Alternatively, exterior layer 20 may be composed of a reinforced hydrogel to provide added durability and resistance to tearing. In this case the hydrogel may be reinforced by any biocompatible material including metal and/or plastic. In addition, the reinforcing material may be in the form of fibers woven together to form a fabric that supports the hydrogel. The fibers of this woven mesh may be metal fibers formed of stainless steel, cobalt chrome, titanium or alloys thereof. Alternatively, the fibers may include plastic fibers and/or other synthetic fibers such as Kevlar®, polyester, rayon and acetate containing fibers. The woven material may also be in the form of a molded lattice. The woven material is coated and inundated with hydrogel. To ease implantation of spacer 10, the hydrogel of exterior layer 20 may be in dehydrated form such that exterior layer 20 has a reduced size during insertion. After insertion, the dehydrated hydrogel rehydrates causing exterior layer 20 to expand.

Intermediate layer 22 is formed of a material having a strength and/or hardness greater than that of exterior layer 20. Intermediate layer 22 may be formed of a solid or woven material. Suitable solid materials include metals such as cobalt chrome, stainless steel, titanium, or alloys thereof. Alternatively, the solid material may include surgical grade plastics. Suitable woven materials may be formed of metal fibers, plastic fibers, or synthetic fibers. Exemplary synthetic fibers include Kevlar®, polyester, rayon or acetate fibers. Intermediate layer 22 may be formed of a woven material similar in composition to the woven reinforcing material of exterior layer 20. In this case, the woven material of intermediate layer 22 can achieve a greater strength and/or hardness relative to exterior layer 20 by incorporating a tighter, denser weave of fibers and/or thicker, stronger fibers.

Core layer 24 is the strongest, hardest of the layers and may be formed of a solid or woven material. For instance, core layer 24 may be formed of a rigid plastic or metal that is molded or machined to shape. Suitable metals include, for example, cobalt chrome, stainless steel, titanium, or alloys thereof. Alternatively, core layer 24 may be formed of a woven material formed of metal fibers, plastic fibers, or synthetic fibers. Exemplary synthetic fibers include Kevlar®, polyester, rayon or acetate fibers. To achieve a strength and/or hardness greater than that of intermediate layer 22, the fibers forming core layer 24 may be woven more tightly to form a denser fabric. Alternatively, or in addition, the fibers forming core layer 24 may be thicker and stronger than those forming intermediate layer 22.

The layered spacer of the above-described embodiment may be implanted between the femoral condyle and the tibial plateau to achieve proper spacing between the femur and the tibia and to correct either a varus or valgus presentation in the knee. The relatively resilient outer layers of the spacer provide a cushion for absorbing a portion of the load placed on the knee, thereby providing immediate or rapid pain relief. Meanwhile, the more rigid interior layers help maintain the shape of the spacer and the proper spacing between the bones.

Although the embodiment described above illustrates the spacer as having three layers, it is contemplated that a spacer of the present invention may have any number of layers. Furthermore, it should be understood that each of the layers need not increase in strength and/or hardness moving from exterior layer to core layer, but rather the layers may increase or decrease in strength and/or hardness moving from one layer to the next. The spacer may be formed in any size, shape or thickness to accommodate the patient's spacing needs and to achieve the desired correction. Also, although the exemplary embodiment described above is adapted for use in the knee joint, it should be understood that the spacer of the present invention may be adapted for use in other joints including the hip and ankle. In addition, the present invention may be adapted for use in the spine as an intervertebral spacer.

Figure 3:
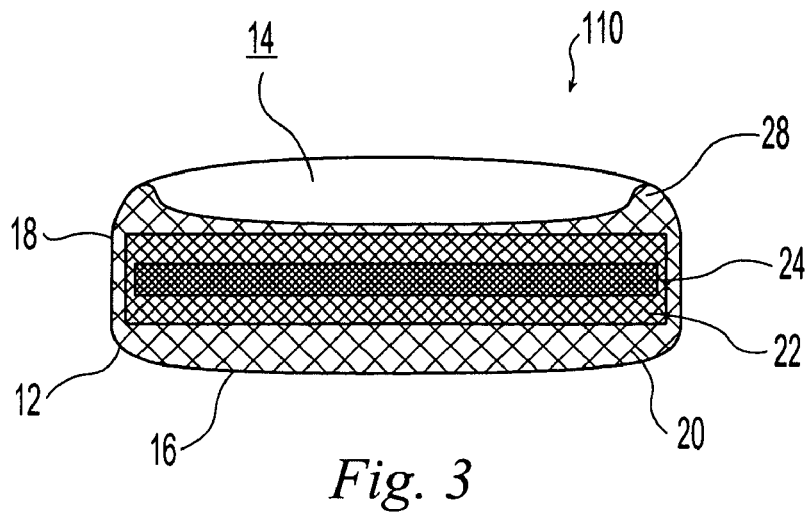
FIG. 3 is a sectional view of the joint spacer implant according to another embodiment of the present invention.

Turning now to FIG. 3, spacer 110 is similar to spacer 10 in that it includes spacer body 12 defined by femoral bearing portion 14, tibial bearing portion 16, and outer periphery 18. Spacer body 110 also includes exterior layer 20, intermediate layer 22 and core layer 24, each having different material properties such that the strength and/or hardness of layers 20, 22 and 24 varies moving from exterior layer 20 to core layer 24. In one embodiment, layers 20, 22 and 24 increase in strength and/or hardness moving from exterior layer 20 to core layer 24.

Spacer 110 also includes lip 28 extending upward from femoral bearing portion 14 and along the outer perimeter of femoral bearing portion 14. Lip 28 limits the movement of spacer 110 within the joint space and prevents spacer 110 from dislocating from the joint space. Lip 28 may be formed of the same material as that of exterior layer 20 or may comprise a different material. Lip 28 may be formed of a resilient material that can deform/compress during insertion to ease placement of spacer 110 in the joint space. For example, lip 28 may be formed of hydrogel.

Figure 6:
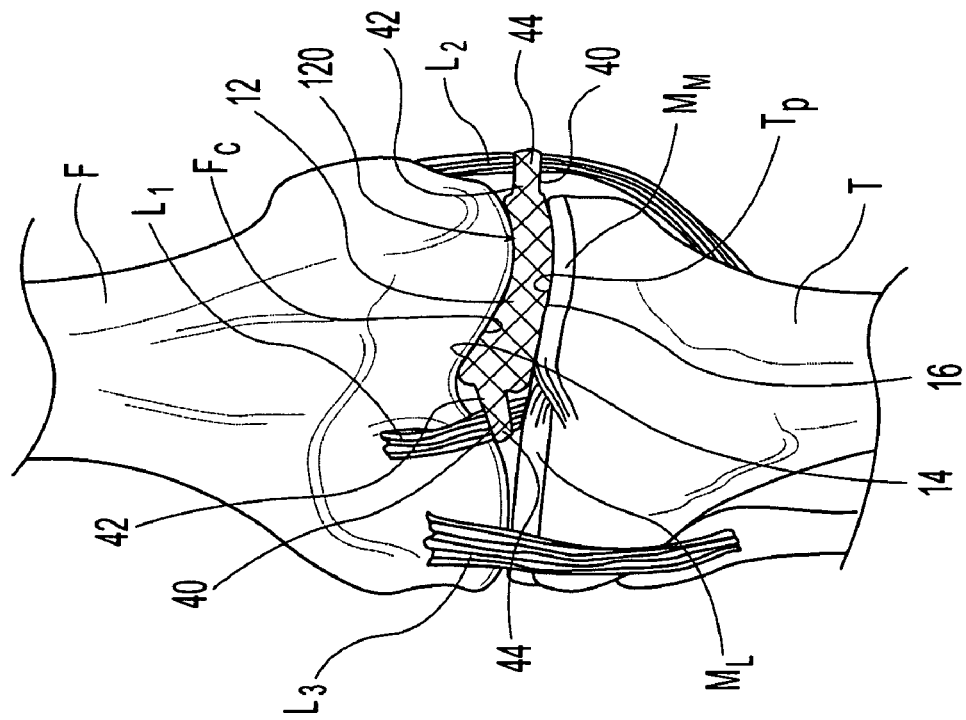
FIG. 6 is an anterior aspect of a knee with a joint spacer positioned between a femoral condyle and the tibial plateau of a knee joint.
Figure 4:
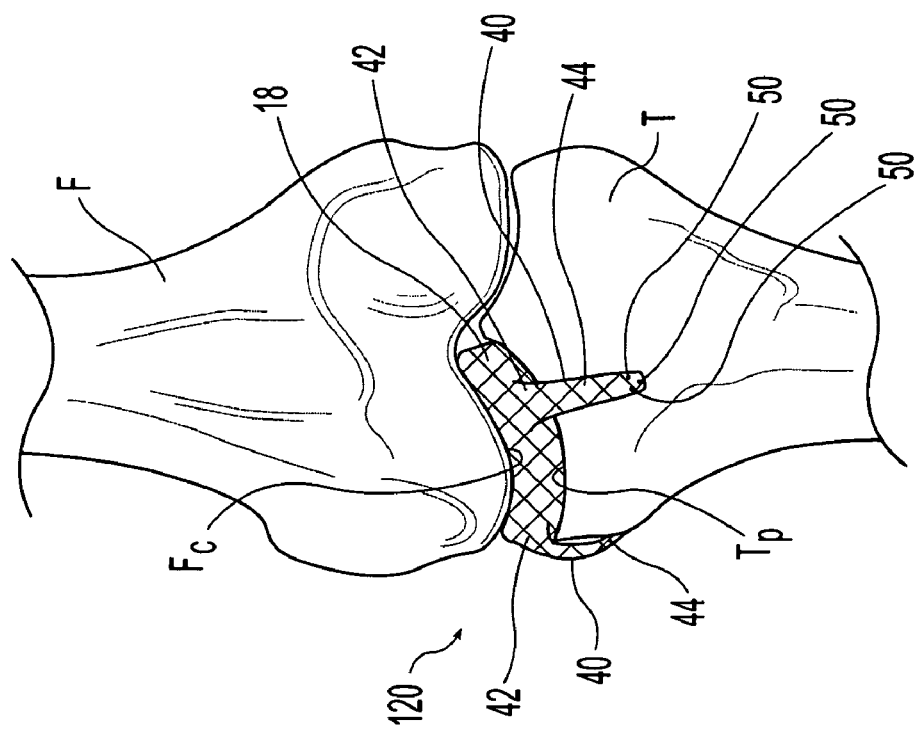
FIG. 4 is an anterior aspect of a knee with a joint spacer implant positioned between a femoral condyle and the tibial plateau of a knee joint.
Figure 5:
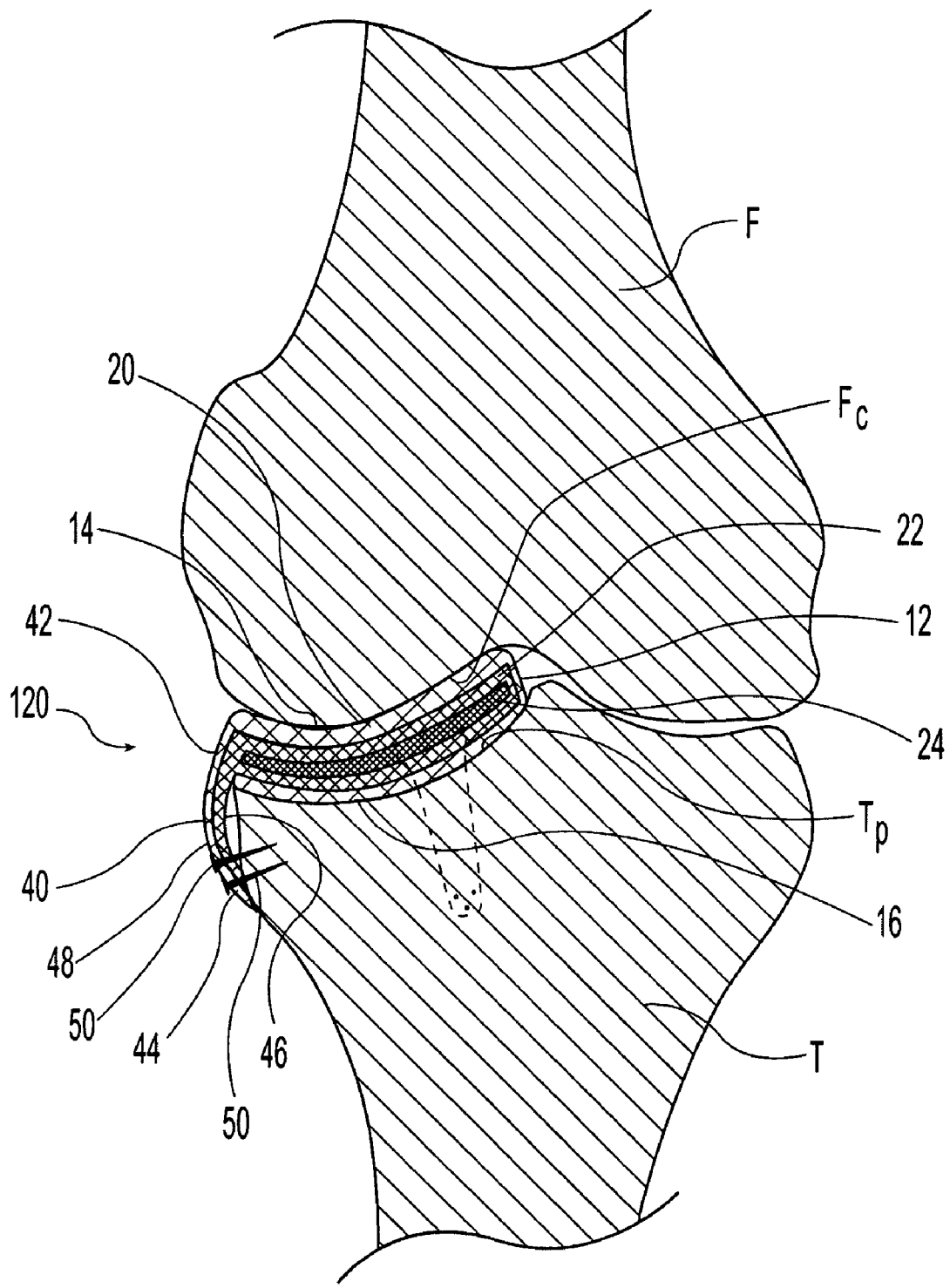
FIG. 5 is a front sectional view of the joint spacer of FIG. 4.

In another embodiment illustrated in FIGS. 4-6, spacer 120 includes spacer body 12 which is defined by femoral bearing portion 14, tibial bearing portion 16, and outer periphery 18 extending about spacer body 12 from femoral bearing portion 14 to tibial bearing portion 16. Spacer body 12 is configured to be positioned between the femoral condyle $F_c$ and tibial plateau $T_p$ such that femoral bearing portion 14 provides an articulating surface for femoral condyle $F_c$ and tibial bearing portion 16 provides an articulating surface for tibia plateau $T_p$. Spacer 120 also includes elongated tethers 40. Each of tethers 40 includes first end 42 coupled to spacer body 12 and second end 44 extending outwardly from outer periphery 18 of spacer body 12. Second end 44 of each of tethers 40 extends outward from between the joint space and is adapted to be fastened to the surface of any component of the joint to thereby limit the mobility of spacer body 12 and prevent dislocation of spacer body 12 from the joint space. For example, as illustrated in FIG. 4, second end 44 of tethers 40 may be fastened to tibia T using fasteners 50. Fasteners 50 may be in the form of sutures, screws, pins, nails, staples or any other suitable fastener.

It should be understood that second end 44 of tethers 40 may be fixed to components of the knee other than the tibia.

For example, as illustrated in FIG. 6, second end of tethers may be fastened to the ligaments of the knee. Spacer 120 is positioned in the medial compartment of the knee between femoral condyle $F_c$ and any remaining medial meniscus $M_m$ of tibial plateau $T_p$. Alternatively, any damaged soft tissue, including the medial meniscus may be removed prior to implantation of spacer 120. Second end 44 of one of tethers 40 is attached to anterior cruciate ligament $L_1$, while second end 44 of the other tether 40 is attached to medial collateral ligament $L_2$. In other alternatives, second end 44 of tethers 40 could also be attached to posterior cruciate ligament (not shown), lateral collateral ligament $L_3$, medial meniscus $M_m$, or lateral meniscus $M_1$.

Tethers 40 are preferably flexible, but strong such that they may be bent into position as shown in FIG. 4. In addition, the tension of the flexible tethers 40 may be adjusted to achieve the desired mobility. In other words, after spacer body 12 is positioned in the joint space, tethers 40 may be pulled taut before attaching to tibia T to provide minimal mobility of spacer body 12. Alternatively, if significant mobility is desired, second end 44 of tethers 40 may be attached to tibia T leaving a little slack in tether 40 to thereby permit movement of spacer body 12 while preventing total dislocation. Furthermore, each of tethers 40 may be fixed with different tensions to provide different levels of mobility in different directions.

Although it is preferable that tethers 40 be flexible, the present invention does contemplate an embodiment in which tethers may be rigid pre-formed structures which are pre-positioned for attachment to the appropriate joint component.

Tethers 40 may be formed either separate from, or integrally as one unit with, spacer body 12. If formed as a separate component, first end 42 of tethers 40 may be coupled either directly or indirectly to spacer body 12 by fastening first end 42 to any part of spacer body 12 using sutures, screws or other types of fasteners. If tethers 40 are formed integrally as one unit with spacer body 12, spacer body 12 and tethers 40 may be formed of plastic molded together in one mold. Differences in flexibility and other characteristics between tethers 40 and spacer body 12 may be achieved in this one piece molding process by providing spacer body 12 and tethers 40 with different thicknesses and/or by adding various curing agents or other compositions to the different sections of the mold.

Spacer body 12 may be a solid, hard construct formed of metal, plastic or other material molded or machined to shape. The solid, hard construct of spacer body 12 may be enveloped with a coating to provide a smooth articulating surface. The coating may comprise hydrogel and/or a ceramic material to provide a slick, smooth surface. Alternatively, spacer body 12 of spacer 120 may be a layered construct resembling spacer body 12 of spacer 10 (FIG. 2) described above.

Turning now to FIG. 5, spacer body 12 of spacer 120 is a layered construct having exterior layer 20, intermediate layer 22, and core layer 24. Tether 40 may be formed integrally with layered spacer body 12 to include all layers 20, 22 and 24. Alternatively, tether 40 may be formed integrally with layered spacer body 12 so as to only include select ones, and/or portions of layers 20, 22 and 24. For instance, tether 40 is integral with spacer body 12 such that intermediate layer 22 and exterior layer 20 bleed out from outer periphery 18 of spacer body 12 to form tether 40. Tether 40 includes bone bearing surface 46 and exterior surface 48. As illustrated in FIG. 5, exterior surface 48 may be formed of an extension of exterior layer 20, thereby providing a smooth, slick surface such that tether 40 will not interfere with the movement of surrounding soft tissues. In contrast, bone bearing surface 46 may be formed of a less smooth material such as an extension of intermediate layer 22. Although not illustrated, it is also contemplated that bone bearing surface 46 at second end 44 of tether 40 may be formed of a bone ingrowth material such as a porous metal or plastic to allow tibia T to grow into second end 44 of tether 40, thereby achieving improved fixation. In addition, bone bearing surface 46 at second end 44 may also include growth factors to further promote the ingrowth of the bone into second end 44 of tether 40.

Spacer 120 is illustrated in FIGS. 4-6 as having two tethers 40. However, the present invention contemplates a spacer having any number of tethers. Furthermore, the tethers may be strategically positioned to extend from any location on the spacer body to facilitate attachment of the tethers to the target joint component. For instance, if it is desired that the spacer body be positioned in the medial component and that the tethers be attached to the anterior cruciate ligament and the medial collateral ligament, tethers may be positioned to extend from both the medial side and anterior side of the spacer body.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A spacer implant for placement between a femoral condyle and a tibial plateau of a knee joint, the knee joint including soft tissue components, the spacer implant comprising:

a spacer body sized and shaped to fit within and substantially occupy a single compartment of the knee joint between the femoral condyle of a femur and the tibial plateau of a tibia, the single compartment of the knee joint extending in a lateral-medial direction from a position near an outermost point of the femoral condyle to a position near an intercondylar notch of the femur and extending in an anterior-posterior direction from a position near an anterior-most point of the femoral condyle to a position near a posterior-most point of the femoral condyle, the spacer body being defined by a femoral concave bearing surface, a tibial bearing surface opposite the femoral concave bearing surface, and an outer periphery extending about the spacer body between the femoral concave and tibial bearing surfaces; and at least one tether extending transversely relative to the spacer body, the at least one tether having a first end coupled to the outer periphery of the spacer body between the femoral concave and tibial bearing surfaces and a second end extending outwardly from the outer periphery of the spacer body to one of a first location above the femoral concave and tibial bearing surfaces for attachment to an outer surface of the femur and a second location below the femoral concave and tibial bearing surfaces for attachment to an outer surface of the tibia wherein the spacer body is formed of a plurality of layers, the plurality of layers including an exterior layer and a core layer, wherein the exterior layer and the core layer have different material properties such that the core layer is greater in strength than the exterior layer.

2. The spacer implant of claim 1 wherein the exterior layer comprises a hydrogel.

3. The spacer implant of claim 1 wherein the core layer comprises a plastic material.

4. The spacer implant of claim 1 wherein the core layer comprises a metal.

5. The spacer implant of claim 1 wherein the plurality of layers include an intermediate layer disposed between the exterior layer and the core layer.

6. The spacer implant of claim 1 wherein the at least one tether is formed integrally as one unit with the spacer body, such that the at least one tether includes at least one of the plurality of layers.

7. The spacer implant of claim 1 wherein the at least one tether includes a plurality of tethers spaced apart from one another along the outer periphery.

8. The spacer implant of claim 1 wherein the at least one tether includes a bone bearing surface, the bone bearing surface comprising a bone ingrowth material.

9. The spacer implant of claim 1 wherein the spacer body is formed of a rigid molded material, and the at least one tether is formed of a flexible material.

10. A spacer implant for placement between a femoral condyle and a tibial plateau of a knee joint, the knee joint including soft tissue components, the spacer implant comprising:
  a spacer body sized and shaped to fit within and substantially occupy a single compartment of the knee joint between the femoral condyle of a femur and the tibial plateau of a tibia, the single compartment extending in a lateral-medial direction from a position near an outer-most point of the femoral condyle to a position near an intercondylar notch of the femur and extending in an anterior-posterior direction from a position near an anterior-most point of the femoral condyle to a position near a posterior-most point of the femoral condyle,
  the spacer body being defined by a femoral concave bearing surface having a first outer edge, a tibial bearing surface opposite the femoral concave bearing surface and having a second outer edge, and an outer periphery extending about the spacer body between the first and second outer edges of the femoral concave and tibial bearing surfaces, the spacer body being formed of a plurality of layers; and
  at least one tether extending transversely relative to the spacer body, the at least one tether having a first end coupled to the spacer body along at least one of the first and second outer edges of the femoral concave and tibial bearing surfaces and a second end extending outwardly from the outer periphery of the spacer body to one of a first location above the femoral concave and tibial bearing surfaces for attachment to an outer surface of the femur and a second location below the femoral concave and tibial bearing surfaces for attachment to an outer surface of the tibia wherein the spacer body is formed of a plurality of layers, the plurality of layers including an exterior layer and a core layer, wherein the exterior layer and the core layer have different material properties such that the core layer is greater in strength than the exterior layer.

11. The spacer implant of claim 10 wherein at least one of the plurality of layers comprises a woven material.

12. The spacer implant of claim 10 wherein the femoral concave bearing surface includes a deformable lip extending upwardly from the femoral concave bearing surface and extending along at least a portion of the outer periphery.

\* \* \* \* \*